US010627365B2

United States Patent
Nishijima et al.

(10) Patent No.: US 10,627,365 B2
(45) Date of Patent: *Apr. 21, 2020

(54) SENSOR CONTROL APPARATUS AND SENSOR CONTROL SYSTEM

(71) Applicant: NGK SPARK PLUG CO., LTD., Nagoya-shi, Aichi (JP)

(72) Inventors: Dai Nishijima, Inuyama (JP); Satoshi Teramoto, Nisshin (JP)

(73) Assignee: NGK SPARK PLUG CO., LTD., Nagoya-shi, Aichi (JP)

( * ) Notice: Subject to any disclaimer, the term of this patent is extended or adjusted under 35 U.S.C. 154(b) by 45 days.

This patent is subject to a terminal disclaimer.

(21) Appl. No.: 16/033,106

(22) Filed: Jul. 11, 2018

(65) Prior Publication Data
US 2018/0321183 A1 Nov. 8, 2018

Related U.S. Application Data

(62) Division of application No. 15/062,596, filed on Mar. 7, 2016, now Pat. No. 10,509,009.

(30) Foreign Application Priority Data

Mar. 9, 2015 (JP) ................................ 2015-046218

(51) Int. Cl.
*G01N 27/419* (2006.01)
*G01N 33/00* (2006.01)

(52) U.S. Cl.
CPC ......... *G01N 27/419* (2013.01); *G01N 33/006* (2013.01)

(58) Field of Classification Search
CPC ............... G01N 27/419; G01N 33/006; G01N 27/406–41; G01N 33/0004–0075
See application file for complete search history.

(56) References Cited

U.S. PATENT DOCUMENTS 4,762,605 A * 8/1988 Tanaka ............... G01N 27/4071
204/406
4,851,103 A * 7/1989 Usami ............... G01N 27/4065
204/406

(Continued)

FOREIGN PATENT DOCUMENTS

| JP | 63-85351 A | 4/1988 |
| JP | 9-257746 A | 10/1997 |
| JP | 5021697 B2 | 9/2012 |

OTHER PUBLICATIONS

Notification of Reasons for Refusal dated Jan. 8, 2018 in corresponding Japanese Application No. 2015-046218.

*Primary Examiner* — Maris R Kessel
*Assistant Examiner* — Joshua L Allen
(74) *Attorney, Agent, or Firm* — Sughrue Mion, PLLC

(57) ABSTRACT

A sensor control apparatus for a gas sensor which detects a particular gas component contained in a gas under measurement. In the case where humidity detection is performed using an electromotive-force-type gas sensor, a sensor control apparatus changes a target voltage of an electromotive force cell to a second target voltage for humidity detection and then to a third target voltage which is lower than a first target voltage which is a target voltage used for detecting the concentration of the particular gas component. In the case where humidity detection is performed using a limiting-current-type gas sensor, the sensor control apparatus changes the voltage applied to a pump cell to a second application voltage for humidity detection and then to a third application voltage which is lower than a first application voltage which is an application voltage used for detecting the concentration of the particular gas component.

2 Claims, 6 Drawing Sheets

(56) References Cited

U.S. PATENT DOCUMENTS

| | | | |
|---|---|---|---|
| 6,007,697 A | 12/1999 | Yagi et al. | |
| 8,495,996 B2* | 7/2013 | Soltis | F02D 41/0025 123/27 GE |
| 2006/0011476 A1* | 1/2006 | Hada | G01N 27/4065 204/406 |
| 2007/0119708 A1* | 5/2007 | Oya | G01N 27/4175 204/401 |
| 2011/0290015 A1* | 12/2011 | Ishida | G01N 27/419 73/335.02 |
| 2013/0319857 A1* | 12/2013 | Ishiguro | G01N 27/4162 204/406 |
| 2015/0013441 A1* | 1/2015 | Aoki | G01N 27/4065 73/114.71 |
| 2015/0268299 A1* | 9/2015 | Umeno | G01N 33/007 324/537 |
| 2016/0061769 A1* | 3/2016 | Hashida | G01N 27/419 204/406 |
| 2016/0208721 A1* | 7/2016 | Wakimoto | G01N 27/4074 |

* cited by examiner

SENSOR CONTROL APPARATUS AND
SENSOR CONTROL SYSTEM

CROSS-REFERENCE TO RELATED
APPLICATIONS

This application is a Rule 53(b) Divisional of U.S. application Ser. No. 15/062,596 filed Mar. 7, 2016, which claims priority based on Japanese Patent Application No. 2015-046218 filed Mar. 9, 2015, the contents of all of which are incorporated herein by reference in their entirety.

BACKGROUND OF THE INVENTION

1. Field of the Invention

The present invention relates to a sensor control apparatus and a sensor control system which detect humidity within a gas under measurement using a gas sensor for detecting a particular gas component contained in the gas under measurement.

2. Description of the Related Art

One of conventionally known sensors used in automobiles is an oxygen gas sensor which is attached to an exhaust passage of an internal combustion engine (e.g., an automotive engine) so as to detect the oxygen concentration of exhaust gas. This oxygen sensor detects the oxygen concentration and thus detects the air-fuel ratio of the exhaust gas by making use of a phenomenon in which the magnitude of current flowing through a sensor element changes with the oxygen concentration of the exhaust gas. A sensor control apparatus which drives the oxygen sensor has a function of energizing and controlling the sensor element, and converting the current flowing through the sensor element to a voltage and outputting the voltage to an electronic control unit (ECU). The ECU obtains the oxygen concentration or air-fuel ratio of the exhaust gas based on an output from the sensor control apparatus. In the ECU, the oxygen concentration or air-fuel ratio of the exhaust gas thus obtained is utilized for air-fuel ratio feedback control such as adjustment of fuel injection amount.

The characteristics of an oxygen sensor mounted on an automobile can possibly change as a result of, for example, deterioration with time or normal wear and tear wherein the sensor output shifts even under the same conditions. In order to solve such a problem, a known technique corrects a change in the characteristics of the oxygen sensor based on the sensor output in an air atmosphere. Also, an air-fuel ratio detection apparatus has been disclosed which detects the humidity of the atmosphere using an oxygen sensor, and renders the correction of the sensor characteristics more accurate in accordance with the humidity (see, for example, Patent Document 1). Here, specific methods for detecting the humidity using an oxygen sensor will be described. In one method in which an oxygen concentration cell utilizing a solid electrolyte body is used, the voltage of an oxygen pump is switched alternatingly between a first preset voltage at which electrolysis of moisture within a gas under measurement does not occur and a second preset voltage at which electrolysis of the moisture within the gas under measurement occurs. The moisture concentration is then determined from the difference between the oxygen pump currents measured in the two cases. In another method in which a two-cell-type oxygen concentration cell is used, the control voltage of the oxygen concentration cell is selectively set to a first preset voltage and a second preset voltage, the oxygen pump currents in the two cases are measured, and the moisture concentration is determined from the difference between the oxygen pump currents (see, for example, Patent Document 2).

[Patent Document 1] Japanese Patent No. 5021697
[Patent Document 2] Japanese Patent Application Laid-Open (kokai) No. S63-85351

3. Problems to be Solved by the Invention

However, in the case where the humidity is very low and the amount of moisture in the atmosphere is small, even when the control voltage is switched to the second preset voltage, the electrolysis of the moisture does not generate a sufficient amount of oxygen ions, and oxygen ions may be pumped out from the metallic oxide of the solid electrolyte body of the oxygen pump cell. In such a case, the metallic oxide of the solid electrolyte body of the oxygen pump cell is reduced, whereby blackening may occur on the solid electrolyte body of the oxygen pump cell. Also, when a high voltage is applied to the solid electrolyte body for a long period of time, the metallic oxide within the solid electrolyte body is reduced and blackening may occur. If blackening occurs on the solid electrolyte body of the oxygen concentration cell, the characteristics (ion conductivity) of the solid electrolyte body deteriorate, and gas detection accuracy and humidity detection accuracy may decrease. Further, if blackening proceeds, the strength of the solid electrolyte body decreases, and cracking may occur.

SUMMARY OF THE INVENTION

The present invention has been accomplished in order to solve the above-described problems, and an object thereof is to provide a sensor control apparatus for a gas sensor which detects a particular gas component contained in a gas under measurement. The sensor control apparatus can accurately measure the particular gas component and humidity by restraining the occurrence of blackening of a solid electrolyte body of the gas sensor. Another object of the present invention is to provide a sensor control system which includes the sensor control apparatus and the gas sensor.

The above objects have been achieved by providing (1) a sensor control apparatus, according to a first mode of the invention, configured for connection to a gas sensor, the gas sensor including an electromotive force cell having a first solid electrolyte body and a pair of first electrodes formed on the first solid electrolyte body and a pump cell having a second solid electrolyte body and a pair of second electrodes formed on the second solid electrolyte body and which detects a particular gas component contained in a gas under measurement. The sensor control apparatus comprises current control means for controlling pump current flowing between the pair of second electrodes such that an electromotive force cell voltage generated between the pair of first electrodes becomes equal to a target voltage; pump current detection means for detecting the pump current; voltage setting means for setting the target voltage to a first target voltage, a second target voltage, and a third target voltage, in this order, the first target voltage being a voltage at which moisture contained in the gas under measurement does not substantially dissociate and which is used when the particular gas component is detected, the second target voltage being a voltage at which moisture contained in the gas under measurement dissociates, and the third target voltage being lower than the first target voltage; and control means for detecting humidity of the gas under measurement based on a difference between the pump current at the time when the target voltage is the first target voltage and the pump current at the time when the target voltage is the second target voltage.

In the sensor control apparatus (1) according to the first mode of the present invention, the target voltage of the electromotive force is set to the first target voltage, the second target voltage, and the third target voltage, in this order, wherein the first target voltage is a voltage at which the moisture contained in the gas under measurement does not substantially dissociate and which is used when the particular gas component is detected, the second target voltage is a voltage at which moisture contained in the gas under measurement dissociates, and the third target voltage is lower than the first target voltage. As a result, the progress of blackening can be delayed, and whereby the particular gas and humidity can be detected accurately. Specifically, in the case where a sufficient amount of oxygen ions are not generated as a result of electrolysis of moisture even when the target voltage is switched to the second target voltage, oxygen ions may be pumped out from metallic oxide constituting the solid electrolyte body of the oxygen pump cell. In such a case, the metallic oxide of the solid electrolyte body of the oxygen pump cell is reduced. However, when the target voltage is then changed to the third target voltage lower than the first target voltage, the pump current flows through the oxygen pump cell in a direction such that oxygen is pumped in, whereby the reduced metallic oxide is oxidized. Thus, it becomes possible to delay the progress of blackening and allow accurate detection of the particular gas and humidity. Notably, the expression "the target voltage is set to the first target voltage and the second target voltage, in this order" means that in the middle of the operation of changing the target voltage from the first target voltage to the second target voltage, the target voltage is not changed to a voltage lower than the first target voltage or a voltage higher than the second target voltage. The expression "the target voltage is set to the second target voltage and the third target voltage is this order" means that in the middle of the operation of changing the target voltage from the second target voltage to the third target voltage, the target voltage is not changed to a voltage higher than the second target voltage or a voltage lower than the third target voltage. Further, the expression "the target voltage is set to the first target voltage, the second target voltage, and the third target voltage, in this order" means that the target voltage is switched (or returned) from the third target voltage to the first target voltage. When the target voltage is returned from the third target voltage to the first target voltage, the target voltage may be immediately returned to the first target voltage or may be gradually returned to the first target voltage. Since detection of the concentration of the particular gas is performed using the first target voltage, when the target voltage is immediately returned to the first target voltage from the third target voltage, regular detection of the concentration of the particular gas can begin earlier.

In a preferred embodiment (2) of the sensor control apparatus according to the first mode (1) of the present invention, the control means causes the pump current detection means to detect the pump current when a predetermined time has elapsed after the target voltage has been changed from the third target voltage to the first target voltage by the voltage setting means.

When the target voltage is returned from the third target voltage to the first target voltage so as to begin regular detection of the concentration of the particular gas, the detection of the pump current is not performed immediately after changing the target voltage until the pump current becomes stable. The gas concentration can be detected accurately by detecting the pump current after elapse of a predetermined time required for the pump current to become stable after the target voltage has been changed to the first target voltage.

The above objects have also been achieved by providing (3) a sensor control apparatus according to a second mode of the invention, configured for connection to a gas sensor, the gas sensor including an oxygen pump cell having a solid electrolyte body, a first electrode formed on one surface of the solid electrolyte body, and a second electrode formed on the other surface of the solid electrolyte body and which detects a particular gas component contained in a gas under measurement. The sensor control apparatus comprises voltage application means for applying a first application voltage, a second application voltage, and a third application voltage, in this order, to the oxygen pump cell, the first application voltage being a voltage at which moisture contained in the gas under measurement does not substantially dissociate and which is used when the particular gas component is detected, the second application voltage being a voltage at which moisture contained in the gas under measurement dissociates, and the third application voltage being lower than the first application voltage; pump current detection means for detecting pump current flowing through the oxygen pump cell; and control means for detecting humidity of the gas under measurement based on a difference between the pump current at the time when the first application voltage is applied to the oxygen pump cell and the pump current at the time when the second application voltage is applied to the oxygen pump cell.

In the sensor control apparatus (3) according to the second mode of the present invention, the first application voltage, the second application voltage, and the third application voltage are applied in this order to the oxygen pump cell, wherein the first application voltage is a voltage at which moisture contained in the gas under measurement does not substantially dissociate and which is used when the particular gas component of the gas under measurement is detected, the second application voltage is a voltage at which the moisture contained in the gas under measurement dissociates, and the third application voltage is lower than the first application voltage. As a result, the progress of blackening can be delayed, whereby the particular gas and humidity can be detected accurately. Specifically, in the case where a sufficient amount of oxygen ions are not generated as a result of electrolysis of moisture even when the second application voltage is applied to the oxygen pump cell, oxygen ions may be pumped out from metallic oxide constituting the solid electrolyte body of the oxygen pump cell. In such a case, the metallic oxide of the solid electrolyte body of the oxygen pump cell is reduced. However, when the third application voltage lower than the first application voltage is then applied to the oxygen pump cell, the pump current flows through the oxygen pump cell in a direction such that oxygen is pumped in, whereby the reduced metallic oxide is oxidized. Thus, it becomes possible to delay the progress of blackening and allow accurate detection of the particular gas and humidity. Notably, the expression "the first application voltage and the second application voltage are applied in this order" means that in the middle of the operation of changing the application voltage from the first application voltage to the second application voltage, a voltage lower than the first application voltage or a voltage higher than the second application voltage is not applied. The expression "the second application voltage and the third application voltage are applied in this order" means that in the middle of the operation of changing the application voltage from the second application voltage to the third application voltage, a voltage higher than the second application voltage or a voltage lower than the third application voltage is not applied. Further, the expression "the first application voltage, the second application voltage, and the third application voltage are applied in this order" means that the application voltage is switched (or returned) from the third application voltage to the first application voltage. When the application voltage is returned from the third application voltage to the first application voltage, the application voltage may be immediately returned to the first application voltage or may be gradually returned to the first application voltage. Since the detection of the concentration of the particular gas is performed using the first application voltage, when the application voltage is immediately returned to the first application voltage from the third application voltage, regular detection of the concentration of the particular gas can begin earlier.

In a preferred embodiment (4) of the sensor control apparatus (3) according to the second mode of the invention, the control means causes the pump current detection means to detect the pump current when a predetermined time has elapsed after the voltage applied to the oxygen pump cell has been changed from the third application voltage to the first application voltage by the voltage application means.

When the application voltage is returned from the third application voltage to the first application voltage so as to begin regular detection of the concentration of the particular gas, the detection of the pump current is not performed immediately after changing the application voltage until the pump current becomes stable. The gas concentration can be detected accurately by detecting the pump current after elapse of the predetermined time required for the pump current to become stable after the application voltage has been changed to the first application voltage.

The above objects of the invention have also been achieved by providing (5) a sensor control system which includes the sensor control apparatus of the first mode or second mode of the invention and the corresponding gas sensor for detecting the particular gas component contained in the gas under measurement.

The sensor control system (5) can accurately measure the particular gas component and humidity of the gas under measurement by using the gas sensor.

4. Effects of the Invention

The sensor control apparatus of the first mode or second mode of the invention provides a sensor control apparatus and a sensor control system which can delay the progress of blackening of the solid electrolyte body even in the case where the humidity is very low and the amount of moisture within the atmosphere is small, or in the case where a high voltage is applied to the solid electrolyte body, and which can accurately measure the concentration of the particular gas component and the humidity.

DESCRIPTION OF REFERENCE NUMERALS

Figure 1:
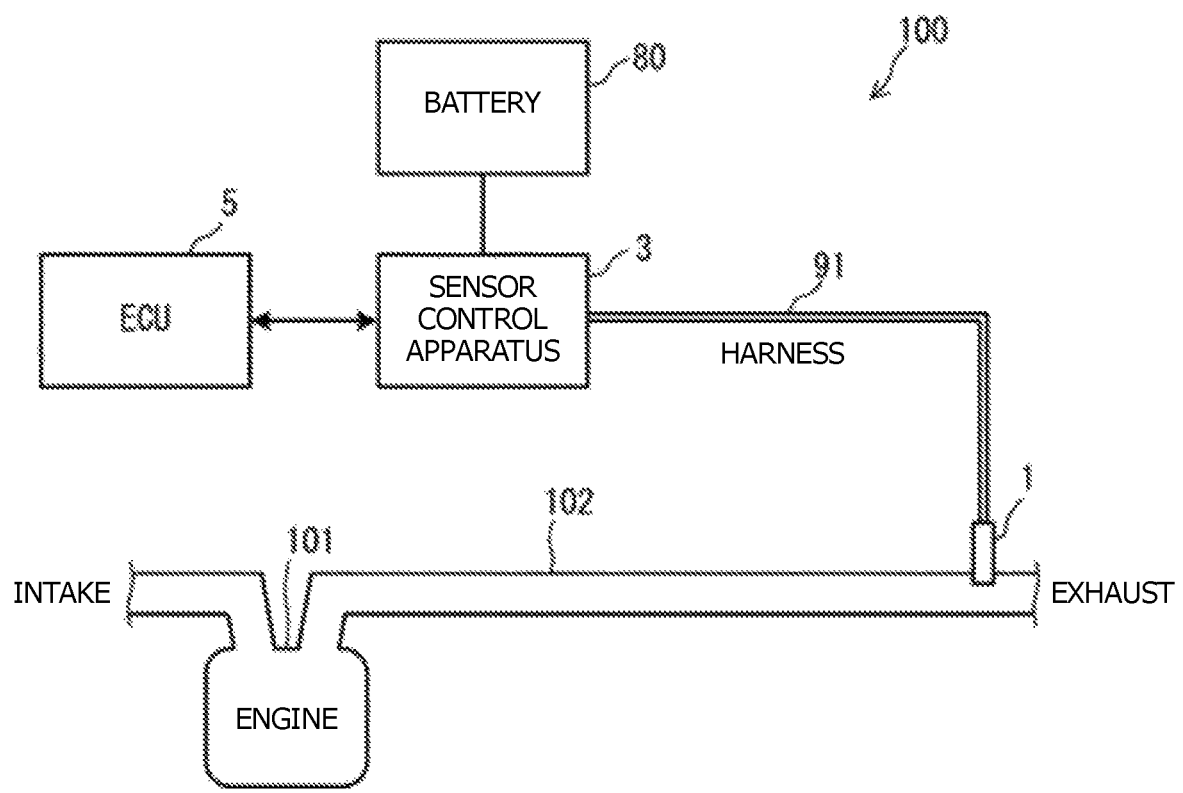
FIG. 1 is a diagram schematically showing the configuration of the exhaust system of an internal combustion engine 100.

Reference numerals used to identify various features in the drawings including the following.
1: full-range air-fuel ratio sensor
3: sensor control apparatus
4: sensor unit
9: microcomputer
10: sensor element
11: solid electrolyte body
13: solid electrolyte body
32: pump current drive circuit
33: voltage output circuit
34: minute current supply circuit
35: reference voltage comparison circuit
36: pump current detection circuit
100: internal combustion engine

DETAILED DESCRIPTION OF THE PREFERRED EMBODIMENTS

The invention will now be described in detail with reference to the drawings. However, the present invention should not be construed as being limited thereto.

First Embodiment

A first embodiment will now be described, embodying a sensor control apparatus and a sensor control system. In the present embodiment, as one example of the sensor control apparatus of the present embodiment, a sensor control apparatus 3 will be described which can detect the oxygen concentration and humidity of a gas under measurement based on a detection signal output from a gas sensor. As one example of the gas sensor, a full-range air-fuel ratio sensor 1 will be described configured such that sensor current changes linearly with oxygen concentration.

An internal combustion engine system 100 includes an engine 101 for propelling an automobile. An exhaust pipe 102 is connected to the engine 101 so as to release exhaust gas discharged from the engine 101 outside the automobile. The full-range air-fuel ratio sensor 1 is disposed in the passage of the exhaust pipe 102. More specifically, the full-range air-fuel ratio sensor 1 is a gas sensor for detecting the concentration of a particular gas component (oxygen in the present embodiment) contained in exhaust gas flowing through the exhaust passage formed by the exhaust pipe 102. The full-range air-fuel ratio sensor 1 is electrically connected, through a harness (signal wire) 91, to the sensor control apparatus 3, which is disposed at a position separated from the sensor. The full-range air-fuel ratio sensor 1 is energized and controlled by the sensor control apparatus 3 so as to detect the oxygen concentration. The sensor control apparatus 3 operates upon receipt of electric power from a battery 80, and outputs to an ECU (engine control unit) 5 a detection signal which represents the oxygen concentration detected through use of the full-range air-fuel ratio sensor 1. The ECU 5 performs air-fuel ratio feedback control for the engine 101 based on the output of the full-range air-fuel ratio sensor 1.

Figure 2:
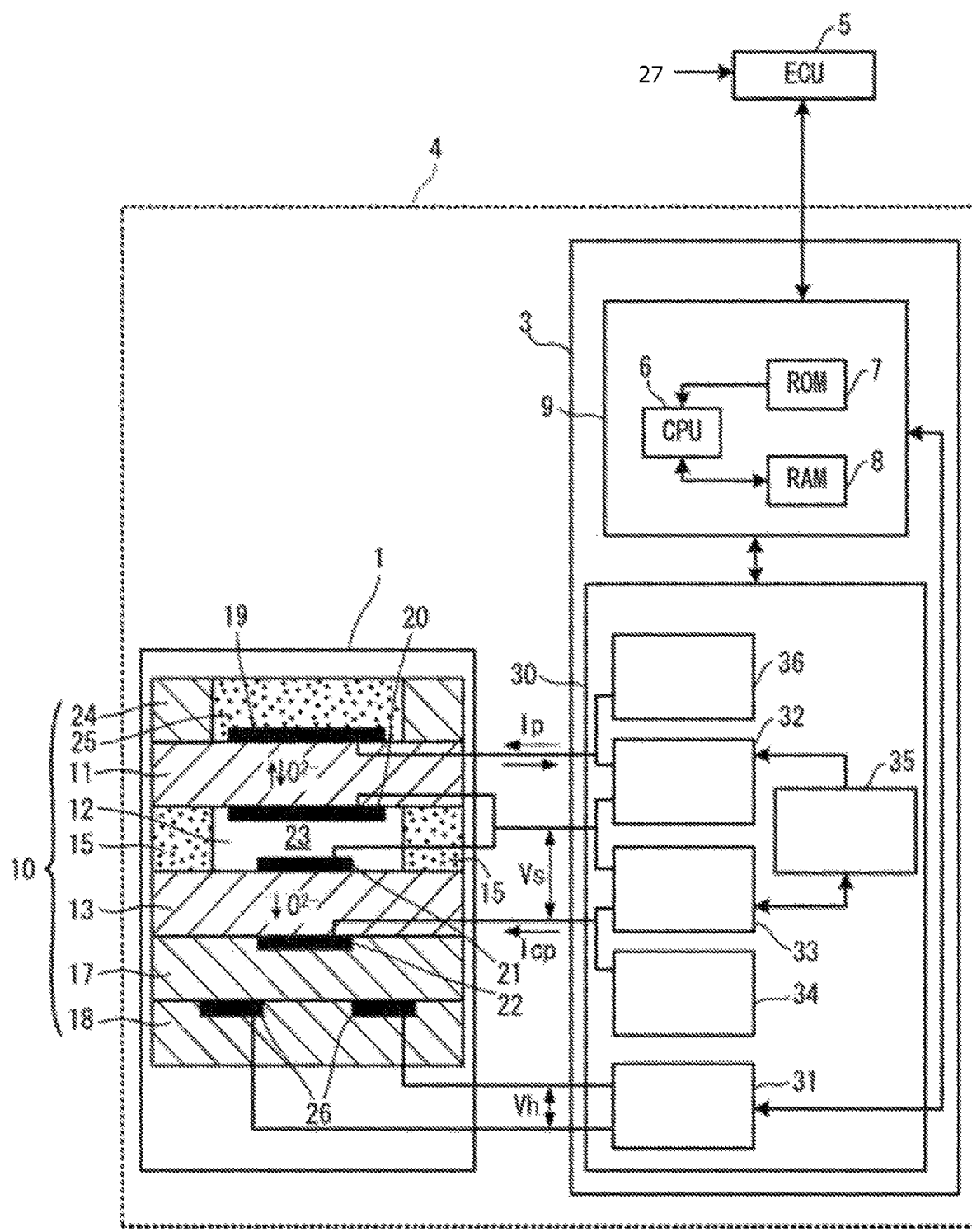
FIG. 2 is a diagram schematically showing the configuration of a full-range air-fuel ratio sensor 1 of a first embodiment.

Next, the details of the full-range air-fuel ratio sensor 1 and the sensor control apparatus 3 will be described with reference to FIG. 2. The full-range air-fuel ratio sensor 1 has a structure in which a thin, long plate-shaped sensor element 10 is held within an unillustrated housing. The full-range air-fuel ratio sensor 1 is electrically connected to the sensor control apparatus 3, which is attached at a position separated from the full-range air-fuel ratio sensor 1, through the harness 91 for taking out the output signal of the sensor element 10 (see FIG. 1).

Notably, the present embodiment shows, as an example, the case where the sensor control apparatus 3 is provided between the full-range air-fuel ratio sensor 1 and the ECU 5, and the full-range air-fuel ratio sensor 1 and the sensor control apparatus 3 constitute a sensor unit 4. The "gas sensor" of the invention corresponds to the full-range air-fuel ratio sensor 1; the "sensor control apparatus" of the invention corresponds to the sensor control apparatus 3 connected to the full-range air-fuel ratio sensor 1; and the "sensor control system" of the invention corresponds to the sensor unit 4. Of course, the manner of disposing the sensor control apparatus 3 can be changed freely. For example, the sensor control apparatus 3 may be incorporated into the ECU 5. In this case, the sensor unit is constituted by the full-range air-fuel ratio sensor 1 and the ECU 5.

First, the structure of the sensor element 10 will be described. The sensor element 10 has a structure in which solid electrolyte bodies 13 and 11 mainly formed of zirconia, and insulating substrates 12, 17, 18 and 24 mainly formed of alumina are stacked in the order of the insulating substrates 18 and 17, the solid electrolyte body 13, the insulating substrate 12, the solid electrolyte body 11 and the insulating substrate 24. A pair of electrodes 19 and 20 mainly formed of platinum are formed on opposite sides of the solid electrolyte body 11. Similarly, a pair of electrodes 21 and 22 are formed on opposite sides of the solid electrolyte body 13. The electrode 22 is sandwiched between the solid electrolyte body 13 and the insulating substrate 17. Each of the solid electrolyte bodies 11 and 13, and the insulating substrates 12, 17, 18 and 24, is formed in the shape of an elongated plate, and FIG. 2 shows cross sections of these members taken perpendicular to the longitudinal direction thereof.

At one end of the insulating substrate 12 with respect to the longitudinal direction thereof, a hollow gas detection chamber 23 is formed, whose opposite wall surfaces are formed by the solid electrolyte bodies 11 and 13 and into which the gas under measurement can be introduced. Porous diffusion-rate-limiting sections 15 are provided at opposite ends of the gas detection chamber 23 with respect to the width direction thereof so as to limit the flow rate of the gas under measurement introduced into the gas detection chamber 23. The electrode 20 on the solid electrolyte body 11 and the electrode 21 on the solid electrolyte body 13 are exposed to the interior of the gas detection chamber 23.

Notably, a heat generation resistor 26 mainly formed of platinum is sandwiched and buried between the insulating substrates 17 and 18. The insulating substrates 17 and 18, and the heat generation resistor 26 function as a heater for activating the solid electrolyte bodies 11 and 13.

The surface of the electrode 19 on the solid electrolyte body 11 is covered with a porous protection layer 25 formed of ceramic (for example, alumina). That is, the protection layer 25 prevents the electrode 19 from deteriorating, which would otherwise be caused by poisoning components, such as silicon, contained in the exhaust gas. The insulating substrate 24 stacked on the solid electrolyte body 11 has an opening so that the insulating substrate 24 does not cover the electrode 19, and the protection layer 25 is provided within the opening.

In the sensor element 10 configured as described above, the solid electrolyte body 11 and the pair of electrodes 19 and 20 provided on the opposite surfaces thereof function as an oxygen pump cell which pumps oxygen into the gas detection chamber 23 from the outside or pumps oxygen out from the gas detection chamber 23 to the outside (hereinafter, the solid electrolyte body 11 and the pair of electrodes 19 and 20 will be collectively referred to as the "Ip cell").

Similarly, the solid electrolyte body 13 and the pair of electrodes 21 and 22 provided on the opposite surfaces thereof function as an oxygen concentration detection cell which generates electromotive force in accordance with the concentration of oxygen between the two electrodes (hereinafter, the solid electrolyte body 13 and the pair of electrodes 21 and 22 will be collectively referred to as the "VS cell"). Also, the electrode 22 functions as an oxygen reference electrode which maintains an oxygen concentration which serves as a reference for detecting oxygen concentration within the gas detection chamber 23. The functions of the Ip cell and the VS cell will be described in detail below.

Next, the configuration of the sensor control apparatus 3 connected to the sensor element 10 will be described. The sensor control apparatus 3 is mainly composed of a microcomputer 9 and an electric circuit section 30. The microcomputer 9 is a microcomputer chip on which a CPU 6, a ROM 7, a RAM 8 (which have known configurations), etc., are mounted. Notably, the ROM 7 stores, for example, a control program for causing the CPU 6 to perform various types of processing.

The electric circuit section 30 is composed of a heater energization control circuit 31, a pump current drive circuit 32, a voltage output circuit 33, a minute current supply circuit 34, a reference voltage comparison circuit 35, and a pump current detection circuit 36.

The heater energization control circuit 31 supplies a voltage Vh to opposite ends of the heat generation resistor 26, while controlling the voltage through PWM (Pulse-Width-Modulation), to thereby cause the heat generation resistor 26 to generate heat, thereby heating the Ip cell and the VS cell. The minute current supply circuit 34 causes a very small current Icp to flow from the electrode 22 of the VS cell to the electrode 21 thereof. As a result, oxygen ions move from the electrode 21 to the electrode 22, whereby an atmosphere having a reference oxygen concentration is produced in the porous electrode 22. Thus, the electrode 22 functions as an oxygen reference electrode, which serves as a reference for detecting the oxygen concentration of the gas under measurement. The voltage output circuit 33 detects the electromotive force VS generated between the electrodes 21 and 22 of the VS cell. The reference voltage comparison circuit 35 compares a predetermined reference voltage with the electromotive force VS detected by the voltage output circuit 33. The reference voltage comparison circuit 35 feeds the comparison result back to the pump current drive circuit 32. Based on the comparison result obtained from the reference voltage comparison circuit 35, the pump current drive circuit 32 controls the magnitude and direction of the pump current Ip flowing between the electrodes 19 and 20 of the Ip cell. As a result, the Ip cell pumps oxygen into the gas detection chamber 23 or pumps oxygen out from the gas detection chamber 23. The pump current detection circuit 36 converts the pump current Ip flowing between the electrodes 19 and 20 of the Ip cell to a voltage and outputs the voltage to the microcomputer 9 as a detection signal.

In the present embodiment, three target voltages (a first target voltage, a second target voltage, and a third target voltage) are used as the reference voltage which is compared with the electromotive force VS by the reference voltage comparison circuit 35. The first target voltage is set to a voltage (e.g., 450 mV) determined such that when the oxygen concentration of the atmosphere within the gas detection chamber 23 is controlled with feedback of the comparison result from the reference voltage comparison circuit 35 to the pump current drive circuit 32, the moisture ($H_2O$) contained in the gas under measurement introduced into the gas detection chamber 23 does not substantially dissociate and the oxygen concentration is measured.

The second target voltage is set to a voltage (e.g., 1000 mV) determined such that when the oxygen concentration of the atmosphere within the gas detection chamber 23 is controlled with feedback of the comparison result from the reference voltage comparison circuit 35 to the pump current drive circuit 32, the moisture ($H_2O$) contained in the gas under measurement introduced into the gas detection chamber 23 dissociates.

The third target voltage is set to a voltage (e.g., 200 mV) determined such that when the oxygen concentration of the atmosphere within the gas detection chamber 23 is controlled with feedback of the comparison result from the reference voltage comparison circuit 35 to the pump current drive circuit 32, the moisture ($H_2O$) contained in the gas under measurement introduced into the gas detection chamber 23 does not substantially dissociate, and oxygen is pumped into the gas detection chamber 23.

At the above-described reference voltage comparison circuit 35, the first target voltage is regularly used as the reference voltage to be compared with the electromotive force VS, and the oxygen concentration of the gas under measurement is calculated based on the pump current Ip. Meanwhile, in the case where the humidity is detected, the second target voltage is used as the reference voltage, and the reference voltage is changed to the third target voltage before it is changed to the first target voltage after detection of the humidity ends. This will be described in detail below. Notably, the pump current drive circuit 32, the voltage output circuit 33, and the reference voltage comparison circuit 35 correspond to the "current control means" of the invention; and the pump current detection circuit 36 corresponds to the "pump current detection means" of the invention. The first reference voltage, the second reference voltage, and the third reference voltage which are compared with the electromotive force VS correspond to the "first target voltage," the "second target voltage," and the "third target voltage," respectively, of the invention.

Next, the configuration of the ECU 5 will be described. The ECU 5 is an apparatus for electronically controlling the operation of the engine 101 of the automobile and other operations. The ECU 5 is a microcomputer on which a CPU, a ROM, a RAM (which have known configurations), etc., are mounted. The ECU 5 controls fuel injection timing and ignition timing by executing a control program. The ECU 5 receives, as information for performing such control, the output (detection signal) from the sensor control apparatus 3 which changes in accordance with the oxygen concentration of the gas under measurement. The ECU 5 also receives, as other pieces of information 27, signals from other sensors (for example, a signal representing crank angle from which the piston position and rotational speed of the engine 101 can be detected, a signal representing coolant temperature, and a signal representing combustion pressure).

Next, the operation of detecting the oxygen concentration of the gas under measurement (the air-fuel ratio of exhaust gas) using the full-range air-fuel ratio sensor 1 will be briefly described. Notably, when the oxygen concentration of the gas under measurement is measured, the first target voltage (e.g., 450 mV) is set (is used) as the reference voltage for comparison by the reference voltage comparison circuit 35. As shown in FIG. 2, the minute current supply circuit 34 first supplies a very small current Icp to the electrode 22 of the VS cell so that the very small current Icp flows toward the electrode 21 thereof. As a result, oxygen contained in the gas under measurement is pumped from the electrode 21 side to the electrode 22 side through the solid electrolyte body 13, and the electrode 22 functions as an oxygen reference electrode. The voltage output circuit 33 detects the electromotive force VS generated between the electrodes 21 and 22. The reference voltage comparison circuit 35 compares the electromotive force VS with the reference voltage. The pump current drive circuit 32 controls the magnitude and direction of the pump current Ip flowing between the electrodes 19 and 20 of the Ip cell based on the result of the comparison by the reference voltage comparison circuit 35 such that the electromotive force VS becomes equal to the reference voltage.

Notably, in the case where the air-fuel ratio of the exhaust gas having flowed into the gas detection chamber 23 is on the rich side of the theoretical air-fuel ratio, since the oxygen concentration of the exhaust gas is low, the pump current Ip flowing between the electrodes 19 and 20 is controlled such that the Ip cell pumps oxygen into the gas detection chamber 23 from the outside. Meanwhile, when the air-fuel ratio of the exhaust gas having flowed into the gas detection chamber 23 is on the lean side of the theoretical air-fuel ratio, since a large amount of oxygen exists in the exhaust gas, the pump current Ip flowing between the electrodes 19 and 20 is controlled such that the Ip cell pumps oxygen out from the gas detection chamber 23 to the outside. The pump current Ip at that time is converted to a voltage by the pump current detection circuit 36, and the voltage is output to the ECU 5, through the microcomputer 9, as the output (detection signal) of the full-range air-fuel ratio sensor 1. At the ECU 5, the oxygen concentration of the gas under measurement (that is, the air-fuel ratio of the exhaust gas) can be determined based on the magnitude and direction of the pump current Ip output from the full-range air-fuel ratio sensor 1.

Figure 3:
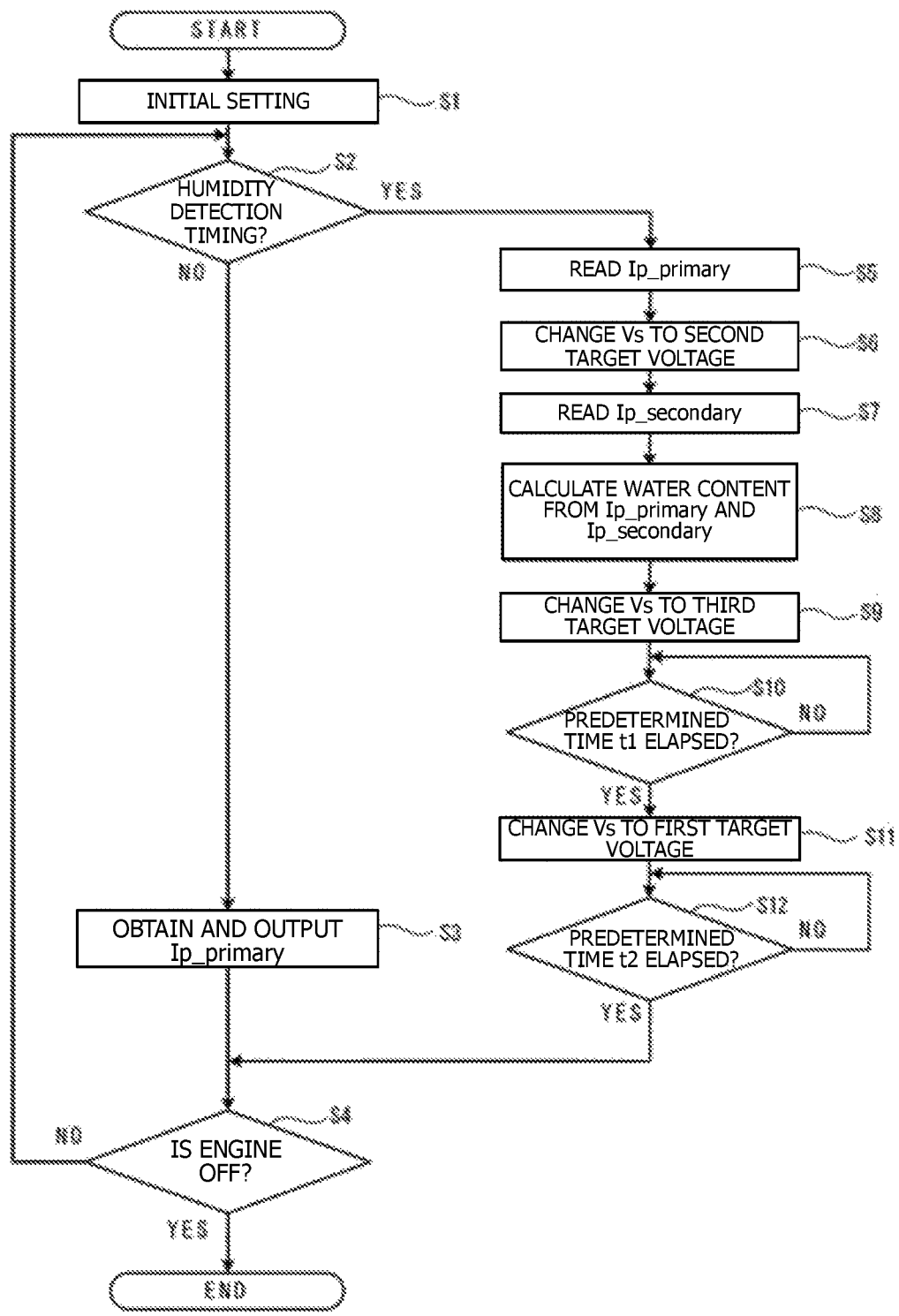
FIG. 3 is a flowchart of main processing executed by a sensor control apparatus 3 of the first embodiment.

Next, the main processing executed in the sensor control apparatus 3 will be described with reference to FIG. 3. A program for executing various types of processing shown in FIG. 3 is also stored in the above-described ROM 7 (see FIG. 2), and is executed by the CPU 6 (see FIG. 2). This main processing is executed at a predetermined timing in a period during which the internal combustion engine 100 is operating. Notably, processing of driving and controlling the heater energization control circuit 31, the pump current drive circuit 32, the voltage output circuit 33, the minute current supply circuit 34, the reference voltage comparison circuit 35, and the pump current detection circuit 36 of the electric circuit section 30 is executed separately from the main processing shown in FIG. 3.

As shown in FIG. 3, when the main processing is started as a result of start of the engine, the CPU 6 performs initial setting of S1 (S stands for step). In the initial setting, the RAM 8 of the microcomputer 9, etc., are initialized, and the reference voltage used by the reference voltage comparison circuit 35 in the sensor control apparatus 3 is set to the first target voltage (e.g., 450 mV).

After completing the initial setting in S1, the CPU 6 proceeds to S2 and judges whether or not humidity detection timing has come. In the present embodiment, the judgment as to whether or not humidity detection timing has come is made by judging whether or not a signal (hereinafter referred to as the "fuel cut signal") indicating that the supply of fuel to the internal combustion engine 100 is stopped has been received.

In the case where the CPU 6 judges in S2 that humidity detection timing has not yet come, the CPU 6 proceeds to S3 so as to perform regular oxygen concentration detection. Specially, through the pump current detection circuit 36, the CPU 6 reads, as "Ip_primary," the pump current Ip flowing between the electrodes 19 and 20 of the Ip cell in a state in which the reference voltage used by the reference voltage comparison circuit 35 is set to the first target voltage (e.g., 450 mV), and outputs Ip_primary to the ECU 5 as the output (detection signal) of the full-range air-fuel ratio sensor 1.

When the processing of S3 ends, the CPU 6 proceeds to S4 and judges whether or not the engine is in a stopped state (i.e., the engine is OFF). In the case where the engine is OFF, the CPU 6 ends the main processing. In the case where the engine is not OFF, the CPU 6 returns to S2.

In the case where the CPU 6 judges in S2 that humidity detection timing has come, the CPU 6 proceeds to S5. In S5, through the pump current detection circuit 36, the CPU 6 reads, as "Ip_primary," the pump current Ip flowing between the electrodes 19 and 20 of the Ip cell in a state in which the reference voltage used by the reference voltage comparison circuit 35 is set to the first target voltage (e.g., 450 mV). The Ip_primary thus read is stored in the RAM 8. Subsequently, the CPU 6 changes the reference voltage used by the reference voltage comparison circuit 35 from the first reference voltage to the second reference voltage (e.g., 1000 mV) (S6).

Subsequently, the CPU 6 proceeds to S7. In S7, through the pump current detection circuit 36, the CPU 6 reads, as "Ip_secondary," the pump current Ip flowing between the electrodes 19 and 20 of the Ip cell in a state in which the reference voltage used by the reference voltage comparison circuit 35 is set to the second target voltage (e.g., 1000 mV). The "Ip_secondary" thus read is stored in the RAM 8. Although not illustrated in FIG. 3, before reading the "Ip_secondary," the CPU 6 may wait until a predetermined time required for the oxygen pump current to become stable has elapsed.

Next, the CPU 6 calculates the moisture content of the gas under measurement from the "Ip_primary" and the "Ip_secondary" stored in the RAM 8 (S8). In S8, the CPU 6 subtracts the "Ip_primary" from the "Ip_secondary" to thereby obtain the difference therebetween; i.e., the difference in the Ip current. This difference in the Ip current indicates the concentration of oxygen originating from the humidity of the gas under measurement (namely, the moisture content of the gas under measurement), and thus detects the humidity of the gas under measurement.

Notably, the "Ip_primary" used in S8 for calculating the moisture content is preferably read in S5 immediately before S6 in which the reference voltage used by the reference voltage comparison circuit 35 is changed from the first target voltage to the second target voltage. This decreases the time difference between the detection timing of the "Ip_primary" and the detection timing of the "Ip_secondary" to thereby avoid a problem of the humidity changing between the time of detecting the "Ip_primary" and detecting the "Ip_secondary."

Next, the CPU 6 proceeds to S9 and changes the reference voltage used by the reference voltage comparison circuit 35 from the second target voltage to the third target voltage (e.g., 200 mV).

After completing the processing of S9, the CPU 6 proceeds to S10 so as to judge whether or not a predetermined time t1 has elapsed. When the predetermined time t1 has elapsed, the CPU 6 proceeds to S11 so as to change the reference voltage from the third target voltage to the first target voltage. The predetermined time t1 is set as a holding time over which the reference voltage must be held at the third target voltage so as to oxidize the reduced metallic oxide of the solid electrolyte body.

After completing the processing of S11, the CPU 6 proceeds to S12 so as to judge whether or not a predetermined time t2 has elapsed after having changed the reference voltage to the first target voltage. When the predetermined time t2 has elapsed, the CPU 6 proceeds to S4, and ends the humidity detection. The predetermined time t2 is set so as to wait, after the reference voltage has been changed to the first target voltage, until the oxygen pump current becomes stable prior to regular detection of the oxygen concentration.

Notably, in the above-described embodiment, the third target voltage is 200 mV. However, the third target voltage may be any voltage lower than the first target voltage, and may be 0 V. The third target voltage and the predetermined time t1 may be determined, by performing a test in advance, in accordance with the magnitude of the second target voltage, the time over which the second target voltage is maintained, and the material and thickness of the solid electrolyte bodies of the gas sensor element. The predetermined time t1 may be determined such that the lower the third target voltage, the shorter the predetermined time t1.

In order to confirm the effect of the present invention, a comparative durability test was carried out for each of the case where the reference voltage was set to the second target voltage and the third target voltage, and the case where the reference voltage was set to the first target voltage and the second target voltage only.

Figure 4:
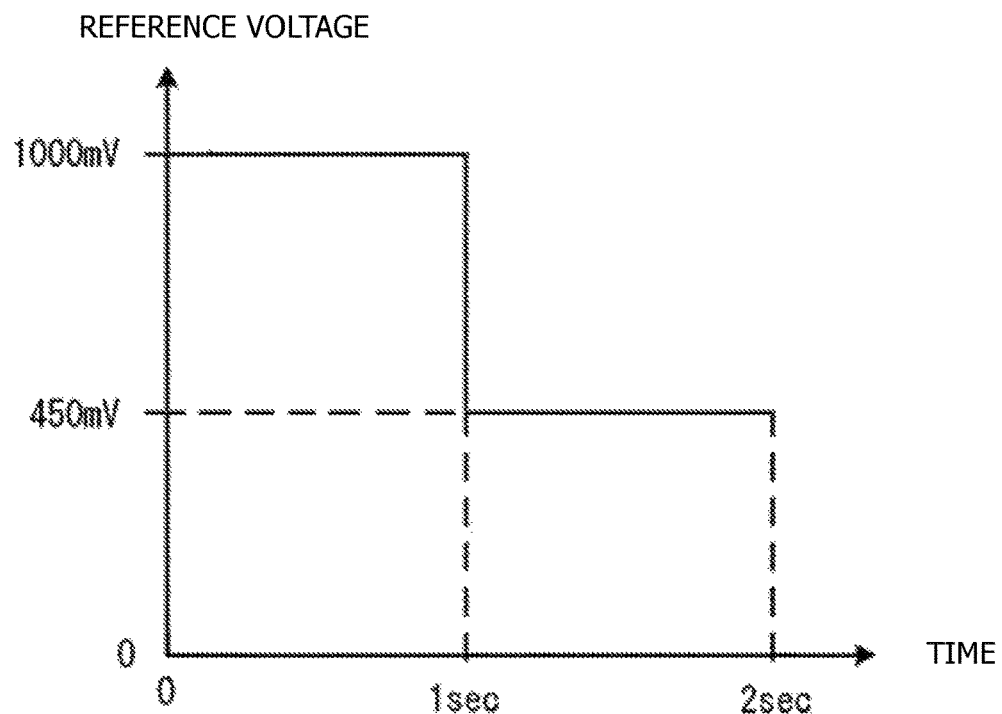
FIG. 4 is a chart showing a change in target voltage with time in the Comparative Example.
Figure 5:
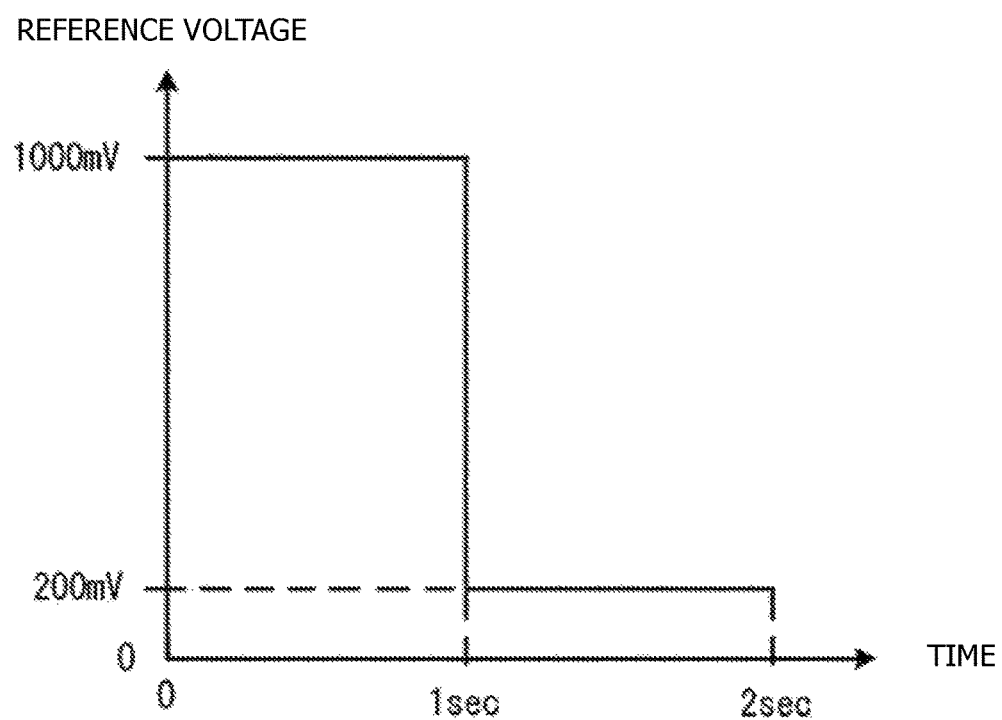
FIG. 5 is a chart showing a change in target voltage with time in the Example.

A durability test was carried out by repeating 3000 times an operation cycle in which the reference voltage used by the reference voltage comparison circuit 35 was changed in accordance with the pattern shown in FIG. 4 (Comparative Example). Also, a durability test was carried out by repeating 3000 times an operation cycle in which the reference voltage used by the reference voltage comparison circuit 35 was changed in accordance with the pattern shown in FIG. 5 (Example). The durability tests of the Comparative Example and Example were carried out under the same conditions, except for the changing pattern of the reference voltage. In order to evaluate the characteristics of the sensor element, the ratio of change between the sensor output before the durability test and the sensor output after the durability test was measured under the following conditions. A four-cylinder engine was operated at a rotational speed of 2500 rpm. Of the four cylinders, three cylinders were controlled by stoichiometric air-fuel ratio control, and fuel was injected into the remaining one cylinder in an amount 30% greater than the amount of fuel supplied by the stoichiometric control. In this state, the oxygen concentration of exhaust gas was measured using the sensor element of the Comparative Example and the sensor element of the Example. As a result of the 30% rich control performed for one cylinder only, the sensor output current indicated that the oxygen concentration varies at a frequency of about 30 Hz. The amplitude of this variation was defined as a response strength of the sensor. With the response strength before the durability test taken as 100%, the response strength after the durability test was obtained, and the absolute value of the difference between the response strength before the durability test and the response strength after the durability test was used as a response strength deterioration rate. Namely, when the response strength after the durability test is 80%, the response strength deterioration rate becomes 20%. It is understood that the smaller the response strength deterioration rate, the smaller the response deterioration. Table 1 shows the response strength deterioration rates of the Comparative Example and the Example after the above-described durability test.

TABLE 1

|  | Response strength deterioration rate |
| --- | --- |
| Example | 2% |
| Comparative Example | 16% |

As understood from Table 1, whereas the response strength deterioration rate in the Comparative Example was 16%, the response strength deterioration rate in the Example was 2%, which is quite smaller than that of Comparative Example.

Second Embodiment

Figure 6:
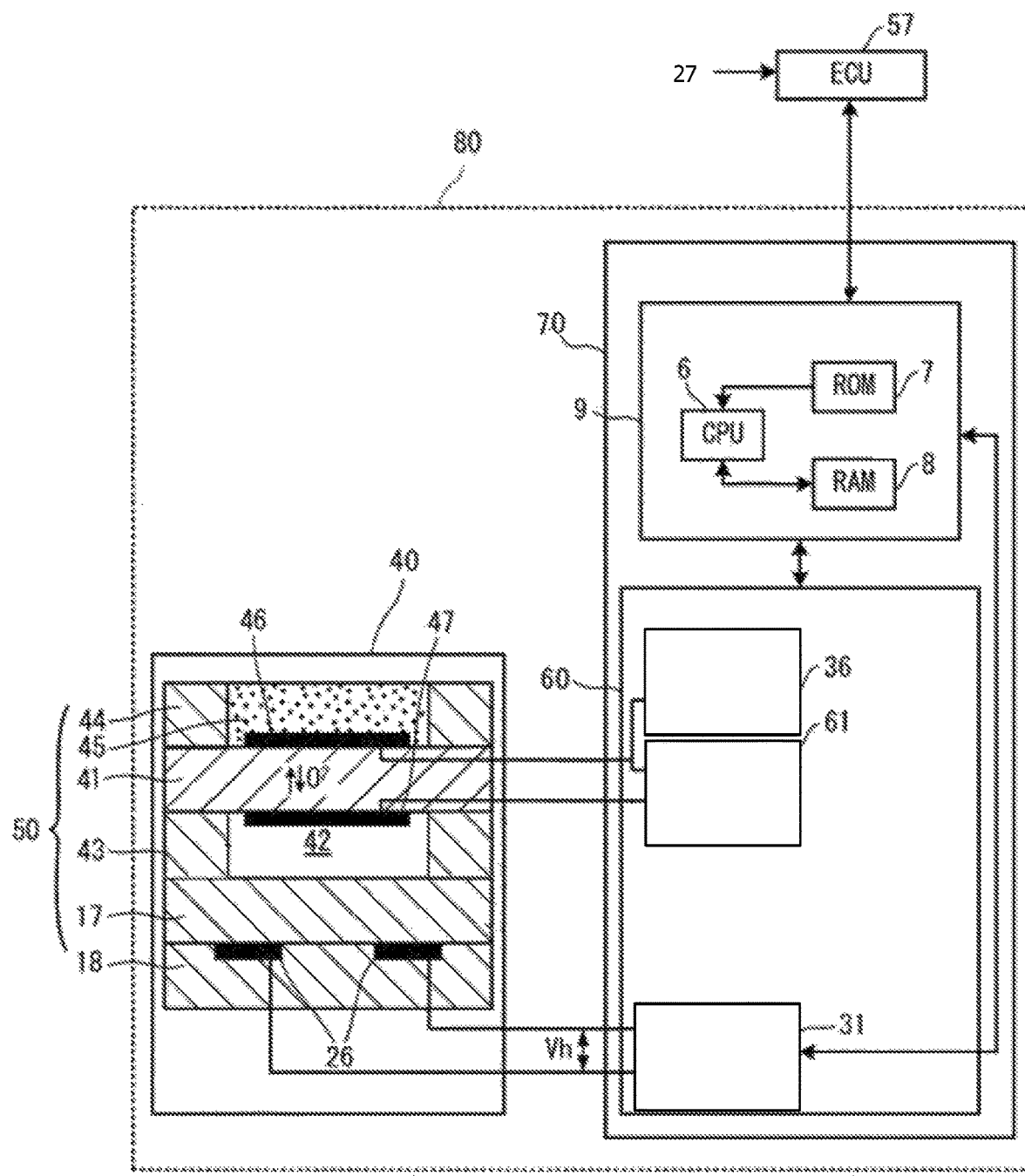
FIG. 6 is a diagram schematically showing the configuration of a limiting-current-type sensor 40 of a second embodiment.

A second embodiment in which the gas concentration/humidity detection apparatus of the present invention is embodied will be described with reference to FIG. 6. In the first embodiment, the gas sensor element is a two-cell-type gas sensor element which has an oxygen pump cell and a reference cell. In contrast, in the second embodiment, the gas sensor element is a so-called limiting-current-type gas sensor element which has a single cell. The present embodiment is identical with the first embodiment except for the gas sensor element and the sensor control apparatus. Only those portions which differ from the first embodiment will be described below. Notably, in the drawings, portions identical with those of the first embodiment are denoted by the same reference numerals as those used in the first embodiment.

The details of a limiting-current-type sensor 40 and a sensor control apparatus 70 will be described with reference to FIG. 6. The limiting-current-type sensor 40 has a structure in which a thin, long plate-shaped sensor element 50 is held within an unillustrated housing. The limiting-current-type sensor 40 is electrically connected to the sensor control apparatus 70, which is attached at a position separated from the limiting-current-type sensor 40, through a harness (not shown) for taking out the output signal of the sensor element 50.

Notably, the present embodiment shows as an example, the case where the sensor control apparatus 70 is provided between the limiting-current-type sensor 40 and the ECU 5, and the limiting-current-type sensor 40 and the sensor control apparatus 70 constitute a sensor unit 80. The "gas sensor" of the invention corresponds to the limiting-current-type sensor 40; the "sensor control apparatus" of the invention corresponds to the sensor control apparatus 70 connected to the limiting-current-type sensor 40; and the "sensor control system" of the invention corresponds to the sensor unit 80. Of course, the manner of disposing the sensor control apparatus 70 can be freely changed. For example, the sensor control apparatus 70 may be incorporated into the ECU 5. In this case, the sensor unit is constituted by the limiting-current-type sensor 40 and the ECU 5.

First, the structure of the sensor element 50 will be described. The sensor element 50 has a structure in which a solid electrolyte body 41 mainly formed of zirconia, and insulating substrates 44, 43, 17 and 18 mainly formed of alumina are stacked in the order of the insulating substrates 18 and 17, the insulating substrate 43, the solid electrolyte body 41, and the insulating substrate 44. A pair of electrodes 46 and 47 mainly formed of platinum are formed on opposite sides of the solid electrolyte body 41. Each of the solid electrolyte body 41, and the insulating substrates 44, 43, 17 and 18 is formed in the shape of an elongated plate, and FIG. 6 shows cross sections of these members taken perpendicular to the longitudinal direction thereof.

At one end of the insulating substrate 43 with respect to the longitudinal direction thereof, a hollow gas detection chamber 42 is formed, whose one wall surface is formed by the solid electrolyte body 41 and into which the gas under measurement can be introduced. Insulating spacers which define the gas detection chamber 42 are provided at opposite widthwise ends of the gas detection chamber 42. The insulating spacers have gas introduction holes (not shown) for introducing the gas under measurement into the gas detection chamber 42 while limiting the flow rate of the gas under measurement. Notably, the electrode 47 on the solid electrolyte body 41 is exposed to the interior of the gas detection chamber 42.

Notably, a heat generation resistor 26 mainly formed of platinum is sandwiched and buried between the insulating substrates 17 and 18. The insulating substrates 17 and 18, and the heat generation resistor 26 function as a heater for activating the solid electrolyte body 41.

The surface of the electrode 46 on the solid electrolyte body 41 is covered with a porous protection layer 45 formed of ceramic (for example, alumina). That is, this protection layer 45 prevents the electrode 46 from deteriorating, which would otherwise be caused by poisoning components, such as silicon, contained in the exhaust gas. The insulating substrate 44 stacked on the solid electrolyte body 41 has an opening so that the insulating substrate 44 does not cover the electrode 46, and the protection layer 45 is provided within the opening.

In the sensor element 50 configured as described above, the solid electrolyte body 41 and the pair of electrodes 46 and 47 provided on the opposite surfaces thereof function as an oxygen pump cell which pumps oxygen into the gas detection chamber 42 from the outside or pumps oxygen out from the gas detection chamber 42 to the outside (hereinafter, the solid electrolyte body 41 and the pair of electrodes 46 and 47 will be collectively referred to as the "Ip cell"). The function of the Ip cell will be described in detail below.

Next, the configuration of the sensor control apparatus 70 connected to the sensor element 50 will be described. The sensor control apparatus 70 is mainly composed of a microcomputer 9 and an electric circuit section 60. The microcomputer 9 is a microcomputer chip on which a CPU 6, a ROM 7, a RAM 8 (which have known configurations), etc., are mounted. Notably, the ROM 7 stores, for example, a control program for causing the CPU 6 to perform various types of processing.

The electric circuit section 60 is composed of a heater energization control circuit 31, a pump voltage application circuit 61, and a pump current detection circuit 36.

The heater energization control circuit 31 supplies a voltage Vh to opposite ends of the heat generation resistor 26, while controlling the voltage through PWM, to thereby cause the heat generation resistor 26 to generate heat, thereby heating the Ip cell. The pump voltage application circuit 61 applies a predetermined voltage between the electrodes 46 and 47 of the Ip cell. The pump current detection circuit 36 detects the pump current Ip flowing between the electrodes 46 and 47 of the Ip cell when the predetermined voltage is applied, converts the detected pump current to a voltage, and outputs the voltage to the microcomputer 9 as a detection signal.

In the present embodiment, three application voltages (a first application voltage, a second application voltage, and a third application voltage) are used as a voltage which is applied by the pump voltage application circuit 61. The first application voltage is set to a voltage (e.g., 450 mV) determined such that the moisture ($H_2O$) contained in the gas under measurement introduced into the gas detection chamber 42 does not substantially dissociate, and the limiting current corresponding to the oxygen concentration within the gas detection chamber 42 can be measured.

The second application voltage is set to a voltage (e.g., 1000 mV) determined such that the moisture ($H_2O$) contained in the gas under measurement introduced into the gas detection chamber 42 dissociates, and the limiting current corresponding to the oxygen concentration within the gas detection chamber 42 can be measured.

The third application voltage is set to a voltage (e.g. 200 mV) determined such that the moisture ($H_2O$) contained in the gas under measurement introduced into the gas detection chamber 42 does not substantially dissociate, and oxygen is pumped into the gas detection chamber 42.

At the above-described pump voltage application circuit 61, the first application voltage is ordinarily used, and the oxygen concentration of the gas under measurement is calculated based on the pump current Ip. Meanwhile, in the case where the humidity is detected, the second application voltage is used, and the application voltage is changed to the third application voltage before it is changed to the first application voltage after the detection of the humidity ends. This will be described in detail below. Notably, the pump voltage application circuit 61 corresponds to the "voltage application means" of the invention; and the pump current detection circuit 36 corresponds to the "pump current detection means" of the invention.

Next, the operation of detecting the oxygen concentration of the gas under measurement (the air-fuel ratio of exhaust gas) using the limiting-current-type sensor 40 will be briefly described. When the oxygen concentration of the gas under measurement is measured, the first application voltage (e.g., 450 mV) is set (is used) in the pump voltage application circuit 61. When the first application voltage is applied, a limiting current corresponding to the concentration of oxygen present within the gas detection chamber 42 flows as a pump current. The pump current detection circuit detects the pump current and outputs it to the microcomputer 9 as a signal corresponding to the oxygen concentration.

Notably, the pump current Ip at that time is converted to a voltage by the pump current detection circuit 36, and the voltage is output to the ECU 5, through the sensor control apparatus, as the output (detection signal) of the limiting-current-type sensor 40. At the ECU 5, the oxygen concentration of the gas under measurement (that is, the air-fuel ratio of the exhaust gas) can be determined based on the magnitude of the pump current Ip output from the limiting-current-type sensor 40.

Next, the main processing executed in the sensor control apparatus 70 will be described with reference to FIG. 7. The difference between the main processing of the first embodiment (FIG. 3) and the main processing of the second embodiment is as follows. In the first embodiment, the reference voltage is switched among the first target voltage, the second target voltage, and the third target voltage. In contrast, in the second embodiment, the voltage applied to the oxygen pump cell is switched among the first application voltage, the second application voltage, and the third application voltage.

Figure 7:
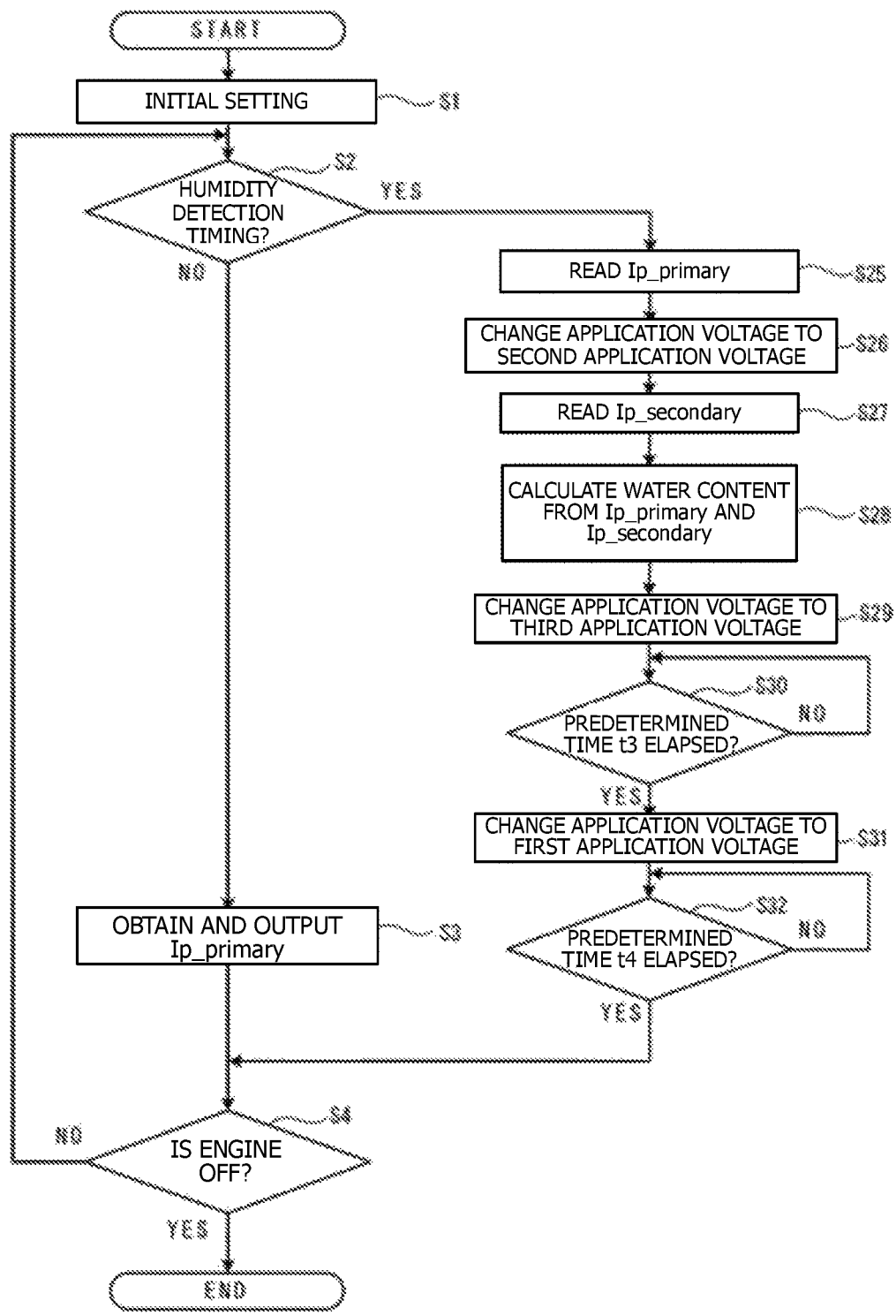
FIG. 7 is a flowchart of main processing executed by a sensor control apparatus 70 of the second embodiment.

As shown in FIG. 7, the CPU 6 initially sets the sensor control apparatus 70 (S1), and judges whether or not humidity detection timing has come (S2).

In the case where the CPU 6 judges in S2 that humidity detection timing has come, the CPU 6 proceeds to S25. In S25, through the pump current detection circuit 36, the CPU 6 reads, as "Ip_primary," the pump current Ip flowing between the electrodes 46 and 47 of the Ip cell in a state in which the voltage applied by the pump voltage application circuit 61 is the first application voltage (e.g., 450 mV). The Ip_primary thus read is stored in the RAM 8. Subsequently, the CPU 6 changes the voltage applied by the pump voltage application circuit 61 from the first application voltage to the second application voltage (e.g., 1000 mV) (S26).

Subsequently, the CPU 6 proceeds to S27. In S27, through the pump current detection circuit 36, the CPU 6 reads, as "Ip_secondary," the pump current Ip flowing between the electrodes 46 and 47 of the Ip cell in a state in which the voltage applied by the pump voltage application circuit 61 has been changed from the first application voltage to the second application voltage. The "Ip_secondary" thus read is stored in the RAM 8.

Next, the CPU 6 calculates the moisture content of the gas under measurement from the "Ip_primary" and the "Ip_secondary" stored in the RAM 8 (S28). In S28, the CPU 6 subtracts the "Ip_primary" from the "Ip_secondary" to thereby obtain the difference therebetween; i.e., the difference in the Ip current. This difference in the Ip current indicates the concentration of oxygen originating from the humidity of the gas under measurement (namely, the moisture content of the gas under measurement), and thus detects the humidity of the gas under measurement.

Notably, the "Ip_primary" used in S28 for calculating the moisture content is preferably read in S25 immediately before S26 in which the voltage applied by the pump voltage application circuit 61 is changed from the first application voltage to the second application voltage. This decreases the time difference between the detection timing of the "Ip_primary" and the detection timing of the "Ip_secondary" to thereby avoid a problem of the humidity changing between the time of detecting the "Ip_primary" and detecting the "Ip_secondary."

Next, the CPU 6 proceeds to S29 and changes the voltage applied by the pump voltage application circuit 61 from the second application voltage to the third application voltage (e.g., 200 mV).

After completing the processing of S29, the CPU 6 proceeds to S30 so as to judge whether or not a predetermined time t3 has elapsed. When the predetermined time t3 has elapsed, the CPU 6 proceeds to S31 so as to change the application voltage from the third application voltage to the first application voltage. The predetermined time t3 is set as a holding time over which the application voltage must be held at the third application voltage so as to oxidize the reduced metallic oxide of the solid electrolyte body.

After completing the processing of S31, the CPU 6 proceeds to S32 so as to judge whether or not a predetermined time t4 has elapsed after having changed the application voltage to the first application voltage. When the predetermined time t4 has elapsed, the CPU 6 proceeds to S4, and ends the humidity detection. The predetermined time t4 is set so as to wait, after the application voltage has been changed to the first application voltage, until the oxygen pump current becomes stable prior to regular detection the oxygen concentration.

The third application voltage may be any voltage lower than the first application voltage, and may be 0 V. The third application voltage and the predetermined time t3 may be determined, by performing a test in advance, in accordance with the magnitude of the second application voltage, the time over which the second application voltage is maintained, and the material and thickness of the solid electrolyte body of the gas sensor element. The predetermined time t3 may be determined such that the lower the third application voltage, the shorter the predetermined time t3.

Notably, the present invention is not limited to the above-described embodiments, and may be modified in various ways without departing from the scope of the invention. In the above-described embodiments, the object is humidity detection for correcting the characteristics of an oxygen sensor in accordance with the humidity of the atmosphere detected through use of the oxygen sensor, and the humidity detection is performed at the timing of fuel cut. However, the humidity detection may be performed at any timing, for example, when the engine of the vehicle is started.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

What is claimed is:

1. A sensor control apparatus configured for connection to a gas sensor, the gas sensor including an oxygen pump cell having a solid electrolyte body, a first electrode formed on first surface of the solid electrolyte body, and a second electrode formed on a second surface of the solid electrolyte body and which detects a particular gas component contained in a gas under measurement, the sensor control apparatus comprising:

voltage application means for applying a first application voltage, a second application voltage, and a third application voltage, in this order, to the oxygen pump cell, the first application voltage being a voltage at which moisture contained in the gas under measurement does not substantially dissociate and which is used when the particular gas component is detected, the second application voltage being a voltage at which moisture contained in the gas under measurement dissociates, and the third application voltage being lower than the first application voltage;

pump current detection means for detecting pump current flowing through the oxygen pump cell;

control means for detecting humidity of the gas under measurement based on a difference between the pump current when the first application voltage is applied to the oxygen pump cell and the pump current when the second application voltage is applied to the oxygen pump cell, wherein the control means causes the pump current detection means to detect the pump current when a predetermined time has elapsed after the third application voltage is changed to the first application voltage by the voltage application means, and wherein the first, second, and third application voltages are positive voltages.

2. A sensor control system comprising: a gas sensor which includes an oxygen pump cell having a solid electrolyte body, a first electrode formed on a first surface of the solid electrolyte body, and a second electrode formed on a second surface of the solid electrolyte body; and the sensor control apparatus as claimed in claim 1.

* * * * *